United States Patent [19]

Means et al.

[11] Patent Number: 4,900,719

[45] Date of Patent: Feb. 13, 1990

[54] NITROSOTHIOLS AS HYPOTENSIVE AGENTS

[75] Inventors: Gary E. Means, Columbus, Ohio; Jeen W. Park, Albany, Calif.

[73] Assignee: The Ohio State University, Columbus, Ohio

[21] Appl. No.: 228,441

[22] Filed: Aug. 5, 1988

[51] Int. Cl.$^4$ .......................... C07K 5/08; A61K 37/02
[52] U.S. Cl. ........................................ 514/18; 530/331
[58] Field of Search .................... 514/18; 530/331, 363

[56] References Cited

PUBLICATIONS

Ignarro, et al., FEBS Letters, 110(2):275–278, 1980.
Craven et al., Biochem. Biophys. Acta, 745: 310–321, 1983.
Saville, Analyst, 83, 670–672, 1958.
Biochemical and Biophysical Research Communications, vol. 94, No. 1, pp. 93–100, Guanylate Cyclase Activation by Nitroprusside and Nitrosoguanidine is Related to Formation of S–Nitrosothiol Intermediates, Louis J. Ignarro et al.
Biochemica et Biophysica Acta, 631(1980) pp. 221–231, "Requirements of Thiols for Activation of Coronary Arterial Guanylate Cyclase by Glyceryl Trinitrate and Sodium Nitrite-Possible Involvement of S–Nitrosothiols", Louis J. Ignarro and Carl A. Gruetter.
The Journal of Pharmacology and Experimental Therapeutics, vol. 218, No. 3, 1981, pp. 739–749, "Mechanism of Vascular Smooth Muscle Relaxation by Organic Nitrates, Nitrites, Nitroprusside and Nitric Oxide; Evidence for the Involvement of S–Nitrosothiols as Active Intermediates", Louis J. Ignarro et al.
The New England Journal of Medicine, Dec. 12, 1985, p. 1548.
"Formation of N–Nitrosoamines from Sodium Nitroprusside and Secondary Amines", Jean Woo Park and Gary E. Means, Biochemical and Biophysical Research Communications, vol. 152, No. 2, pp. 916–920, Apr. 29, 1988, "Reaction of S–Nitrosoglutathione with Sulfhydryl groups in Protein", Jean Woo Park.

*Primary Examiner*—Howard E. Schain
*Assistant Examiner*—Susan M. Perkins
*Attorney, Agent, or Firm*—Frank H. Foster

[57] ABSTRACT

Systemic arterial pressure of an animal is decreased by administering directly to the animal an S-nitroso therapeutic compound, and particularly any of the S-nitrosoglutathione, D-(S-nitroso)-3-mercaptomethylpropionyl-L-proline, or S-nitrosothiol serum albumin in a dosage amount effective for a desired decrease and being an amount preferably between about 7 to 10 µg/kg. animal weight/minute.

3 Claims, 2 Drawing Sheets

NITROSOTHIOLS AS HYPOTENSIVE AGENTS

This invention relates to decreasing systemic arterial pressure in an animal by administering directly to the animal an S-nitroso therapeutic agent for that purpose. More particularly, the invention concerns the preparation of certain nitrosothiol compounds, including preparation in relatively stable form, and their administration directly to decrease systemic arterial pressure and/or decrease hypertension, and especially the compounds of S-nitrosoglutathione, D-(S-nitroso)-3-mercapto methylpropionyl)-L-proline, and S-Nitrosothiol(serum albumin).

BACKGROUND

Sodium nitroprusside, SNP, $[Na_2Fe(CN)_5 NO.2H_2O]$ is a potent, fast acting, intravenous hypotensive agent. It is used to lower blood pressure during hypertensive and cardiac emergencies, for the clinical treatment of malignant hypertension and to lower cardiac back pressure during periods of cardiac insufficiency (Pharmacology of Antihypertensive Drugs, Ed.-A. Scriabine, Raven Press, N.Y., 1980, "Sodium Nitroprusside", V. A. W. Kreye, pg. 373–396) and for inducing "controlled hypotension" during many different types of surgery.

It acts specifically on the vascular smooth muscles, affecting their relaxation and thereby, vasodilation and lower cardiac back pressure. Its full effects are expressed in less than a minute, persist until infusion is terminated and dissipate within five to ten minutes (Tinker, J. H. & Cucchiara, R. F., Int. Anesthes. Clin. 16, 89, 1978).

Considering the wide popularity of SNP and the fact that it has been available for over half a century, surprisingly little is known about its molecular pharmacology. At the present time there is considerable evidence supporting the hypothesis that relaxation by SNP is mediated through activation of guanylate cyclase [GTP pyrophosphate-lyase (cyclizing), (Rapport, R. M. and Murad, F., J. Cyclic Nucl. Pro. Phos. Rev. 9, 281, 1983)].

There has been controversy about the actual species involved in the activation of guanylate cyclase. Although Arnold et al (Proc. Nat'l. Acad. Sci. USA 74, 32093, 1977 and Mittal and Murad (Proc. Nat'l. Acad. Sci. USA 74, 4360, 1977) demonstrated activation of guanylate cyclase by nitric oxide and suggested that the latter moiety may be the common proximate species mediating SNP, there is no chemical evidence as to how SNP spontaneously, rapidly releases the NO moiety. Other reports (Ignarro et al., FEBS. Lett. 110, 275, 1980, and Craven et al, Biochem. Biophys. Acta 745, 310, 1983) have shown that some S-nitrosothiols, mainly S-nitrosocysteine, which was obtained from the reaction of cysteine with NO gas, activate guanylate cyclase and lower the blood pressure. The chemical and pharmacological mechanisms involved, however, are far from clear. Furthermore, their proposed mechanism which is based on the instability of S-nitrosocysteine and subsequent effects of NO formed upon its breakdown without any chemical evidence, has been recently challenged (Craven, P. S. and DeRubertis, F. R., Biochem. Biophys. Acta 745, 310, 1983).

Sodium nitroprusside (SNP) is administered under careful supervision to effect rapid short-term reductions in blood pressure. The physiological degradation of SNP and can be detected in the blood stream of patients during and after its administration. Cyanide, one product of that degradation, is normally converted by the liver to thiocyanate which is then slowly cleared by the kidneys. Cyanide, especially, and thiocyanate are both very toxic. Their toxicities limit the amounts of SNP that may be safely administered and almost completely preclude its administration to patients with impaired liver or kidney function. Because thiocyanate is a strong inhibitor of thyroxine biosynthesis, SNP is also precluded for patients with thyroid dysfunction.

Accordingly, the development and usage of hypotensive agents or anti-hypertensive drugs, which if used in place of SNP would eliminate the side effects and risks associated with the latter's metabolic degradation to cyanide and thiocyanate, would be highly desirable and provide advantages and a significant advance in the art.

SUMMARY STATEMENT OF THE INVENTION

The invention provides for administration directly by any of diverse suitable means and techniques to animals of S-nitrosoglutathione, D-(S-nitroso)-3-mercaptomethylpropionyl-1-proline, or S-nitrosothiol serum albumin in a dosage effective to decrease the animal's systemic arterial pressure. By means of the invention there is provided a potent fast-acting controlled hypotensive effect in the animal, controllable by being dose dependent and by providing substantially the equivalent effect providable by SNP. By administration according to the invention, resulting various metabolic by-products therefrom advantageously are those, such as to be of natural occurrence in the animal, e.g. glutathione, serum albumin, etc., or to be substances, e.g. Captopril, already approved for administration to animals.

DETAILED DESCRIPTION OF THE INVENTION

Figure 1:
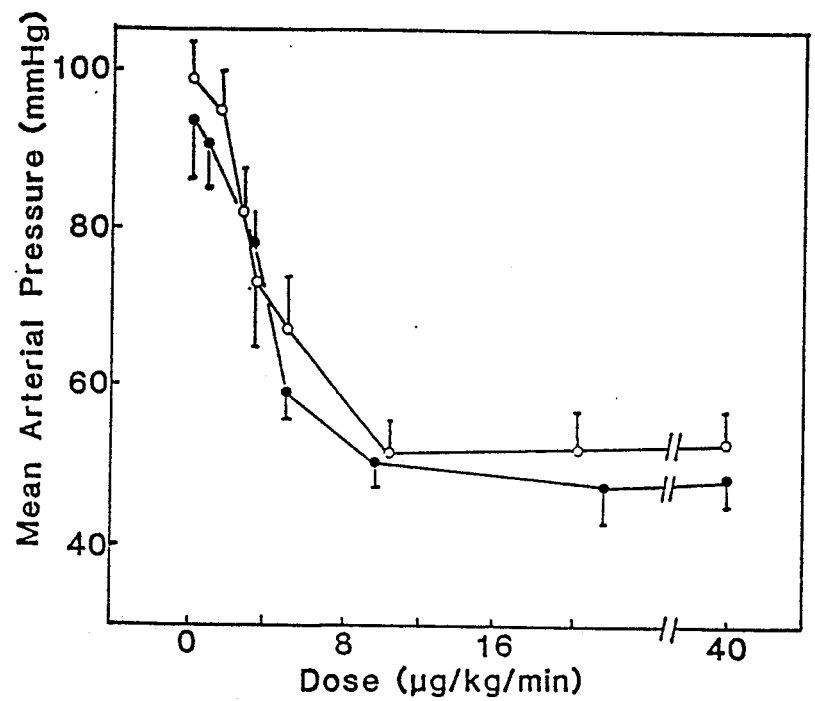
FIG. 1 presents the results in dogs of changes in mean arterial pressure for various venous infusion administered dosages of GSNO and SNP.

To determine how SNP lowers blood pressure, there was studied its effects on a number of compounds normally found in the blood stream. It reacts very rapidly with one of them, glutathione and S-nitrosoglutathione is a product of that reaction. S-nitrosoglutathione (GSNO) and other nitrosothiols are not too well known and very little is known about their chemistry. Accordingly, there were synthesized and characterized GSNO and some other nitrosothiols. Several reactions of nitrosothiols that may be related to the pharmacological mechanism of SNP were studied. On the basis of these studies and in accord with other investigators (Ignarro, L. J., Lipton, H., Edwards, J. C., Baricos, W. H., Hyman, A. L., Kadowitz, P. J., and Gruetter, C. A. (1981) Mechanism of Vascular Smooth Muscle Relaxation by Organic Nitrates, Nitrites, Nitroprusside and Nitric Oxide: Evidence for the Involvement of S-Nitrosothiols as Active Intermediates., J. Pharmacol. Exper. Ther., 218, 739-749), it appeared that S-nitrosoglutathione was an intermediate in the mechanism by which SNP and several other hypotensive drugs (i.e. nitroglycerin, isosorbide dinitrate, etc.) lower blood pressure.

GSNO and some other nitrosothiols can be synthesized relatively easily and for purposes of the invention possess adequate stability. Ignarro and coworkers (supra 1981), for example, have described experiments indicating that nitrosothiols are probably intermediates in the process by which SNP and many other vasodilators lower blood pressure but apparently believe them to be unstable, short-lived intermediates. The particular nitrosothiols they generally employed are relatively unstable. Others, including GSNO which is likely to be the actual intermediate in the mechanism of those drugs, however, have been found to be able to be provided in relatively stable form. GSNO and those others are sufficiently stable, for example, that they are able to be used as hypotensive drugs.

For this application and as reported elsewhere (Ignarro et al, supra, 1981), GSNO is apparently an intermediate in the mechanism by which SNP, nitroglycerin and many other hypotensive drugs lower blood pressure. These other investigators advocate S-nitrosothiols to be potent activators of the enzyme, guanylate cyclase, and there is a large body of evidence indicating that the activation of guanylate cyclase in vascular smooth muscles is linked to their relaxation and the concomitant vasodilation and decreased blood pressure. As the rapidly formed, first intermediate in the pharmacological mechanism of SNP, GSNO herein has been shown to be at least as effective as SNP, and to have the same rapid onset and brief duration.

To demonstrate the involvement of GSNO as an intermediate in the pharmacological mechanism of SNP, the effects of intravenous GSNO on the blood pressure of several animal species was evaluated. In accord with preliminary studies on anesthetized dogs and anesthetized monkeys, GSNO administered directly lowered blood pressure in each of the animals to about the same extent as SNP and the onset and dissipation of its effects were essentially the same as obtained with SNP. These apparently are the first studies showing the effects of GSNO on blood pressure in an animal.

The blood streams of animals contain significant concentrations of glutathione (GSH) and small amounts of many other thiols. The S-nitroso derivative of glutathione (GSNO) and other nitrosothiols undergo rapid transnitrosation reactions in the presence of thiols as follows:

ti GSNO+RSH⇌GSH+RSNO wherein G is a moiety of S-nitrosoglutathione less its —SNO function, and R is a moiety of a plasma protein less a —SH function; and more generally

R'SNO+R"SH⇌R'SH+R"SNO wherein R' and R", both or only one, are G, as just defined preceedingly, and wherein when only one of R' or R" is G then the other R' or R" is a protein, contained in serum plasma, less a thiol (—SH) functional group. In studies not reported here, the degree of the transnitrosation appears to depend on the specific structure of the S-nitroso-compounds and specific thiols involved. Under the conditions employed and the equipment available, the reaction is too fast to follow. Under physiological conditions, the transfer of an NO moiety from GSNO and most other simple nitrosothiols (i.e. RSNO) to glutathione (GSH) would also presumably, be very fast.

This invention contemplates that the introduction of other nitrosothiols into the blood stream could therefore also result in the rapid formation of GSNO and a corresponding thiol (RSH). This advantageously direct administration of GNSO or of certain nitrosothiols other than GSNO may therefore lower blood pressure, essentially the same as with GSNO, and provide specific advantages over both GSNO and SNP. These other nitrosothiols can be more stable, they can be administered the same or differently and/or they can provide slightly differing effects, i.e slower acting and/or longer lasting. The thiol produced upon the reaction of circulating GSH with other nitrosothiols advantageously should not, of course, have any serious, harmful effects.

Two other directly administered nitrosothiols in addition to GSNO, particularly are contemplated to be useful therapeutic agents. They are both easy to synthesize, relatively stable and the thiol that would be produced upon reaction with GSH is believed to have no harmful effects. The first of these is the S-nitroso derivative of human serum albumin. It is quite stable, particularly, when freeze dried and stored at 0°-3° C. The thiol that would result from reaction with nitrososerum albumin would be serum albumin, a protein that is already present in the blood stream and has no harmful effects. Like GSNO and SNP, it would need to be given intravenously, but its reaction with GSH is slower than that of GSNO and it might therefore be slower acting and longer lasting.

Another contemplated useful nitrosothiol is S-nitrosocaptopril, D-(S-nitroso) 3-mercaptomethylpropionyl-L-proline, as shown below. It is

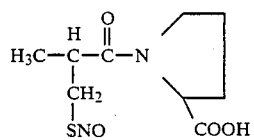

the S-nitroso derivative of a widely used drug captopril (Capoten ®, a proprietary product of Squibb Pharmaceutical Co., Princeton, N.J.) that is used to treat high blood pressure. According to "The Merck Index" Captopril also is known by the names of "1-(3-Mercapto 2-methyl-1-oxopropyl)-L-proline; (2S)-1-(3-mercapto-2-methylpropionyl)-L-proline; D-2-methyl-3-mercaptopropanoyl-L-proline; SQ 14225; Capoten: Lopirin. $C_9H_{15}NO_3S$: mol wt 217.28. C 49.75%, H 6.96%, N 6.45%, O 22.09%, S 14.75%." Its S-nitroso derivative is quite stable, the thiol that would result upon reaction with GSH would be captopril which may have beneficial effects itself and, at least, is not harmful. It is considered that the S-nitroso derivative of captopril might be more convenient to administer than either of the previously described nitrosothiols. The need to administer SNP and, presumably, GSNO and nitrososerum albumin intravenously limits their use. It is contemplated possible to administer more lipophilic nitrosothiols, like the S-nitroso derivative of captopril, topically, transdermally or even orally. This would be much more convenient, would allow for possible self-administration and would result in a slower and longer lasting effect. To lower arterial pressure by infusion administration a practical effective dosage is about 7 μg/1 kg. Animal weight/ minute and preferably are between 7 to 10 μg/1 kg/min. for the following example 2 and 3 S-nitroso therapeutic agents, respectively, S-nitrosocaptopril and S-nitroso derivative of human serum albumin.

EXAMPLE 1

Preparation of GSNO from GSH with sodium nitrite (a) GSNO was prepared as according to Saville (Analyst 83 670 (1958)) with slight modification, by dropwise addition of HCl to a solution containing equimolar amounts of GSH and sodium nitrite until a pH of 1.5 was attained. After standing for 5 min. at room temperature, the red GSNO solution was neutralized with NaOH. GSNO has absorption maxima at 544 ($\epsilon=15.0$ M$^{-1}$ cm$^{-1}$) and 332 ($\epsilon=750$ M$^{-1}$ cm$^{-1}$).

(b) Alternatively, for the preparation of solid GSNO, a minimum amount of water was added to an equimolar amount of glutathione (reduced form) and sodium nitrite and the resulting solution was then adjusted to pH 1.5 with 6 M HCl. The red solution was rapidly frozen in a dry ice-acetone bath and then washed several times with cold absolute ethanol. The residue was dried under vacuum.

The yield of solid GSNO, a pink powder, prepared by the above mentioned method, was greater than 90%, as determined by high-performance liquid chromatography and by visible (VIS) spectroscopy, from the absorption at its maximum at 544 nm. The only other product identified was oxidized form of glutathione.

Confirmation of the identity of GSNO was obtained by infrared (IR) spectroscopy and fast atom bombardment mass spectrometry (FAB/MS). The IR spectrum was obtained on a Beckmann Model 4220 IR spectrophotometer with a NaCl cell and Nujol as a mulling agent. The peak characteristic of the sulfhydryl moiety in the reduced form of glutathione ($\sim$2540 cm$^{-1}$) was absent from the IR spectrum of GSNO and a peak indicative for a nitroso moiety was identified at 1450 cm$^{-1}$.

The FAB mass spectrum was obtained on a Kratos MS-30 mass spectrometer fitted with an Ion Tech B-11 NF Saddle field atom gun. The FAB source was operated at room temperature with a Xenon gas flow of about 0.5 cm$^3$min$^{-1}$ at 10 psi, giving a beam at 8 KeV of 1 mA. The solid form of GSNO was mixed with glycerol and then coated on the probe. FAB is a soft ionization method that produces cationized molecular ion and fragment ions from nonvolatile and thermally labile substances. FAB enables the analysis of nanomole amounts of GSNO of high molecular weight without the need for prior chemical derivatization which may destroy sensitive functional groups. The FAB mass spectrum of GSNO crystal dissolved in glycerol exhibits an abundant molecular ion [M+H]$^+$ at m/z 337, sodium cationized molecular ion [M+Na]$^+$ at m/z 359, and [M+H−NO]$^+$ at m/z 307 as characteristic fragments. The spectrum contained numerous intense peaks related to oligomers of glycerol and its related sodium cationized ions, which are normal background for FAB.

Although crystals of S-nitrosothiols other than S-nitroso-N-acetylpenicillamine have been reported to be highly unstable in air and at room temperature (L. J. Ignarro et al., Biochem. & Biophys. Res.Comm., (1980), Vol. 94, No. 1, pp. 93-100), the prepared solid form of GSNO is quite stable, much more stable than solutions of GSNO. In air at 4° no change in the characteristic original absorbance at 544 nm was observed after 32 days. At room temperature, 75% of that absorption remained after the same period. Exclusion of light and air had virtually no noticeable effect on the stability of solid GSNO upon storage for more than 30 days.

Animal experiments

Fifty milligrams of SNP (Nipride, Roche Laboratories) was reconstituted in 250 ml of 5% dextrose in water. A GSNO solution was diluted as 50 ug/ml in 5% dextrose in water. Seven mongrel dogs (18.1–31.8 kg) and seven cynomologus monkeys (Macaca fascicularis; 4.4–9.0 kg) were used in the study. The animals were given a pre-anesthetic (monkeys—Ketamine HCl, 10 mg/kg I.M.; dogs—0.2 mg/kg fentanyl and 1 mg/kg droperidol, Innovar Vet I.V.) and anesthetized with a mixture of α-chloralose (50 mg/kg) and urethane (500 mg/kg) given as an intravenous injection. The left femoral artery and vein were cannulated with heparinized saline-filled catheters. Arterial pressure was obtained from the arterial catheter using an electromedics MS-20 solid state pressure transducer and recorded on a Gould 2400 chart recorder. Randomized venous infusions of GSNO (n=7) and SNP (n=5) were made using Harvard apparatus compact infusion pump model 976. The infusion was maintained until a new steady state value for mean arterial pressure had been obtained for each infusion rate. The infusion rate was varied over the following ranges: GSNO 1.5–38.9 μg/kg/min (8 levels) and SNP 1.7–43.8 μg/kg/min (6 levels).

Results on the anesthetized dogs and monkeys showed that GSNO significantly lowered blood pressure in each of the animals to about the same extent as SNP and that the onset and dissipation of its effect were essentially the same as obtained with SNP.

Figure 2:
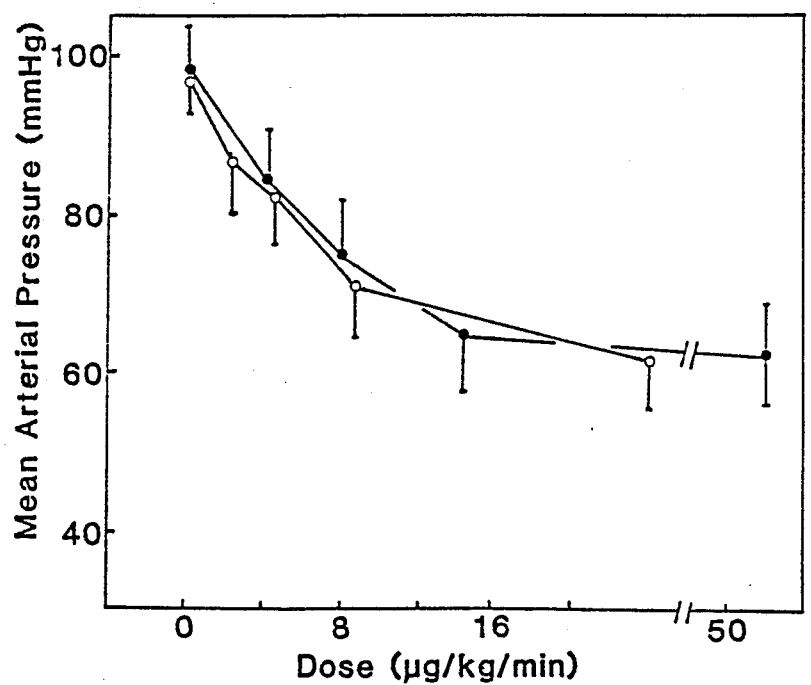
FIG. 2 presents the results in monkeys of changes in mean arterial pressure for various venous infusion administered dosages of GSNO and SNP.

Intravenous administrations of GSNO or SNP in a wide range of doses decreased systematic arterial pressure in a dose related fashion. FIGS. 1 and 2 show the dose-response curves for the dogs and monkeys, respectively, that occurred by SNP or GSNO administrations. In each figure (.) presents the data for SNP and (o) presents the data for GSNO. The blood pressure lowering effect of SNP and GSNO is greater in monkeys than in dogs. When 20 μg/kg/min of SNP or GSNO was administered, mean arterial pressure decreased 35–40 torr for dogs and 45 torr for monkeys. The noted response time for SNP was about 28.6±2.5 sec. and for GSNO about 33.4±6.0 sec.

From the collected animal data, it can be noted that in general the decrease in blood pressure is dosage dependent. By infusion administration to significantly lower arterial pressure an effective dosage of GSNO should be at least about 7 μg/1 kg animal weight/minute and dosages greater than about 10 μg/1 kg/min. are not necessary with preferred practical infusion dosages being of between about 7 to 10 μg/1 kg/min.

EXAMPLE 2

Preparation of S-Nitrosocaptopril 50 mg of Captopril (0.236 mMoles) was dissolved in 10 ml of 0.1 M HCl at room temperature and cooled briefly in an ice bath. A total of 0.25 ml of 1 M NaNO$_2$ was then added in several small portions with rapid swirling. After 2 min on ice, 1.0 ml of 0.5 M Na$_2$HPO$_4$ was added and the solution was adjusted to pH 7.3 with 0.1 M NaOH. The solution displayed absorption maxima at 542 nm (E=19.8 M$^{-1}$cm$^{-1}$) and 330 nm (E=995 M$^{-1}$cm$^{-1}$).

Animal Experiments

By following in general the procedure described for GSNO in Example 1, animal experiments are performed on a plurality of anesthetized dogs with each intravenous injection of S-Nitrosocaptopril in dextrose as well as the arterial blood pressure of the dogs being recorded. Significant lowering of arterial blood pressure in the dogs is observed from the injections, although the employed amounts of S-Nitrosocaptopril in the injections and the observed lowering of the blood pressure are not necessarily the same and/or the equivalent as with GSNO in the Example 1 animal experiments.

EXAMPLE 3

Preparation of S-nitroso derivative of human serum albumin 100 mg of human serum albumin ($1.49 \times 10^{-3}$ nMoles) was dissolved in 10 ml of 0.05 M phosphate buffer, pH 6.8 and cooled in an ice bath. A small volume of 3-mercaptopropionic acid (0.01 ml; ~0.08 mMoles) were dissolved in 1.0 ml of 0.1 M HCl, cooled in an ice bath and 6.9 mg of $NaNO_2$ (0.1 mMoles) were added with rapid swirling. After 1 min, the pink solution was added to the solution of human serum albumin and immediately placed on a $2.5 \times 35$ cm column of Sephadex G-25 and eluted with 0.05 M sodium phosphate buffer, pH 7.3. The protein solution was collected and stored on ice.

Animal Experiments

By following in general the procedure described for GSNO in Example 1, animal experiments are performed on a plurality of anesthetized dogs with the just-prepared S-nitroso derivative human serum albumin being first placed in aqueous dextrose and then intravenously injections into the dogs. The specific injections as well as the arterial blood pressure of the dogs are recorded. Significant lowering of arterial blood pressure in the dogs is observed from the injections, although the employed amounts of S-nitroso derivative of human serum albumin in the injections and the observed lowering of the blood pressure are not necessarily the same and/or the equivalent as with GSNO in the Example 1 animal experiments.

Although the foregoing examples illustrate embodiments of the invention by administration to animals by catherization means and intravenous infusion of a dextrose solution containing the S-nitroso therapeutic agent, other forms and means of administration are contemplated to be useful and may be employed. Contemplated administrations include, for example: an effective dosage of the S-nitroso agent in a dissolvable solid carrier being administered orally, such as sublingually by placement under the tongue; also an effective dosage in a solid or liquid carrier given by mouth, for passage to an internal organ for release, such as parenterally by bolus for stomach ingestion and intraperitonally release of the agent; also topical administering such as by a transdermal patch or the like applied to the epidermis with requisite means, such as carriers and/or membranes for rapid and/or controlled-timed release, as desired, of effective dosage of the S-nitroso agent; transdermal and also intravenous injection administration of the agent in applicable requisite form, e.g. solution, emulsion, etc., and dosage for the desired effect; etc.

It will be apparent to those skilled in the art that numerous changes and improvements can be made in the preferred embodiments of the invention described above without departing from the scope of the invention. Accordingly, the foregoing description is to be construed in an illustrative and not in a limiting sense with the scope of the invention being defined solely by the appended claims.

We claim:

1. A process for decreasing the systemic arterial pressure in an animal which comprises:

administering directly to the animal of an aqueous composition containing S-nitrosoglutathione, which before placing in said aqueous composition had been in a therapeutically pure, relatively stable, solid form, which is characterizable by no change in its characteristic original absorbance at 545 nm upon storage in air for 30 days at 4° C., and whose process of preparation had included reacting in aqueous solution of glutathione with a nitrite and a subsequent freezing with vacuum drying to provide said solid form, in a dosage amount effective for said decreasing and being the amount of at least about 7 µg/kg. animal weight/minute or more.

2. The process of claim 1 wherein the administering is intravenously to the animal and of an aqueous dextrose composition containing the dosage amount between 7 to 10 µg/kg. animal weight/minute.

3. S-nitrosoglutathione as a therapeutically pure relatively stable, solid form characterized by no change in its characteristic original absorbance at 545 nm upon storage in air for more than 30 days at 4° and by a process of preparation which included reacting an aqueous solution of glutathione with a nitrite and a subsequent freezing with vacuum drying to provide said solid form.

* * * * *